United States Patent
Nakagawa et al.

(10) Patent No.: US 7,776,354 B2
(45) Date of Patent: Aug. 17, 2010

(54) REMEDIES FOR GLOMERULAR DISEASES

(75) Inventors: Takashi Nakagawa, Hachioji (JP); Sayaka Toyoizumi, Sayama (JP); Masako Isuge, Higashimurayama (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 684 days.

(21) Appl. No.: 11/434,061

(22) Filed: May 16, 2006

(65) Prior Publication Data

US 2006/0257474 A1 Nov. 16, 2006

Related U.S. Application Data

(63) Continuation of application No. 10/504,851, filed as application No. PCT/JP03/03995 on Mar. 28, 2003, now abandoned.

(30) Foreign Application Priority Data

Mar. 28, 2002 (JP) ............................. 2002-092238

(51) Int. Cl.
*A61K 47/00* (2006.01)

(52) U.S. Cl. ...................... 424/439; 514/929

(58) Field of Classification Search ........................ None
See application file for complete search history.

(56) References Cited

U.S. PATENT DOCUMENTS

| | | | |
|---|---|---|---|
| 4,534,975 | A | 8/1985 | Yamato et al. |
| 5,883,124 | A | 3/1999 | Samid |
| 2001/0036913 | A1* | 11/2001 | Gould et al. .................... 514/2 |
| 2003/0018040 | A1* | 1/2003 | Sugiyama et al. ........... 514/275 |
| 2003/0068374 | A1* | 4/2003 | Kamei et al. ................. 424/468 |
| 2004/0116468 | A1 | 6/2004 | Nakagawa et al. |
| 2004/0116486 | A1 | 6/2004 | Nakagawa et al. |
| 2006/0257474 | A1 | 11/2006 | Nakagawa et al. |

FOREIGN PATENT DOCUMENTS

| | | |
|---|---|---|
| WO | 97/37688 | 10/1997 |
| WO | 99/18952 | 4/1999 |
| WO | WO 01/30353 A1 | 5/2001 |

OTHER PUBLICATIONS

Jones et al. "Glomerular Thrombosis"; American Journal of Pathology; (Oct. 1951); 27(5): pp. 841-855.*
Nakamura et al. Nephrology Dialysis Transplantation (2002) 17: pp. 798-802.*
Gohda et al. Kidney & Blood Pressure Research (2001); 24: pp. 33-38.*
Ogawa, Shigenao et al., "Effects of various antiplatelet drugs and a defibrinating agent on experimental glomerulonephritis in rats", Journal of Laboratory and Clinical Medicine, vol. 99, No. 3, pp. 428 to 441, 1982.
Cameron, J.S. et al., "Coagulation and thromboembolic complications in the nephrotic syndrome", Advances in Nephrology from the Necker Hospital, vol. 13, pp. 75 to 114, 1984.
U.S. Appl. No. 11/574,678, filed Mar. 05, 2007, Nakagawa.
Database Biosis [Online], Database Accession no. PREV 200000404970, XP-002428406, Zhang Yun, "Protective effect of simvastatin for renal function in diabetic nephropathies" p. 1.

* cited by examiner

*Primary Examiner*—Robert A Wax
*Assistant Examiner*—Jeffrey T Palenik
(74) *Attorney, Agent, or Firm*—Oblon, Spivak, McClelland, Maier & Neustadt, L.L.P.

(57) ABSTRACT

The present invention relates to a preventive or therapeutic agent for a glomerular disease which comprises an antithrombocytic agent and an HMG-CoA reductase inhibitor as active ingredients.

The above agent is useful for prevention and therapy of various glomerular diseases including chronic glomerular nephritis.

21 Claims, 1 Drawing Sheet

REMEDIES FOR GLOMERULAR DISEASES

TECHNICAL FIELD

The present invention relates to a preventive or therapeutic agent for a glomerular disease.

BACKGROUND ART

A glomerular disease (primary glomerular nephritis) brought about by causing lesion in a glomerulus of a kidney is clinically classified into any of seven diseases consisting of acute nephritis after infected with hemolytic *streptococcus*, crescentic glomerulonephritis (rapidly progressive nephritis), IgA nephropathy, membranous nephropathy, membranous proliferative nephropathy, focal glomerulonephritis and minimal change nephrotic syndrome. Among them, the diseases other than the acute nephritis after infected with hemolytic *streptococcus*, the crescentic glomerulonephritis and the minimal change nephrotic syndrome are generally called chronic glomerular nephritis, and the cause and the time of onset thereof are relatively indistinct in many cases. Further, the lesion processes thereof is mostly progressive and results in renal failure in many cases.

Medicines which fundamentally heal such glomerular diseases have not yet been found, and agents such as a steroid agent, an anti-thrombocytic agent, an anticoagulant agent and an immunosuppersive agent are used for the purpose of inhibiting or retarding transition to dialysis by drug therapy.

Among them, the anti-thrombocytic agent has a function to inhibit discharge of various mediators such as thromboxane A2, histamine, a leukocyte migrating factor, cytokine and a proliferative factor from a blood platelet, and therefore it is considered that use of the present agent makes it possible to inhibit progressive augmentation of a glomerular disease caused by proliferation of a mesangium cell and a failure in a barrier mechanism in a glomerular snare wall which are brought about by various mediators (Cameron J S et al.: Coagulation and thromboembolic complications in the nephrotic syndrome. Adv Nephrol 13:75, 1984).

Further, it is reported that in a kidney disease, the degree of hyperlipidemia statistically correlates with the degree of proteinuria deterioration or aggravation in renal function, and a hyperlipidemia therapeutic agent such as an HMG-CoA reductase inhibitor is used as well for therapy of a kidney disease for the purpose of removing an augmentative factor of a kidney disease of hyperlipidemia.

However, a kidney disease-improving effect brought about when using an anti-thrombocytic agent and a hyperlipidemia therapeutic agent is limited, and still remains unsatisfactory.

An object of the present invention is to provide a drug exhibiting an excellent effect in prevention or therapy of a glomerular disease.

DISCLOSURE OF THE INVENTION

Intensive researches repeated by the present inventors in view of such situation have resulted in finding that when using an anti-thrombocytic agent in combination with an HMG-CoA reductase inhibitor which is a hyperlipidemia therapeutic agent, a marked nephritis therapeutic effect is shown as compared with a case where the respective drugs are used alone and that it is useful as a preventive or therapeutic agent for a glomerular disease.

That is, the present invention provides a preventive or therapeutic agent for a glomerular disease which comprises an anti-thrombocytic agent and an HMG-CoA reductase inhibitor as active ingredients.

Further, the present invention provides a medicinal composition for prevention or therapy of a glomerular disease, which comprises an anti-thrombocytic agent, an HMG-CoA reductase inhibitor and a pharmaceutically acceptable carrier.

Also, the present invention provides use of an anti-thrombocytic agent and an HMG-CoA reductase inhibitor for producing a preventive or therapeutic agent for a glomerular disease.

Further, the present invention provides a treating method for a glomerular disease, which comprises administering an anti-thrombocytic agent and an HMG-CoA reductase inhibitor.

BEST MODE FOR CARRYING OUT THE INVENTION

Figure 1:
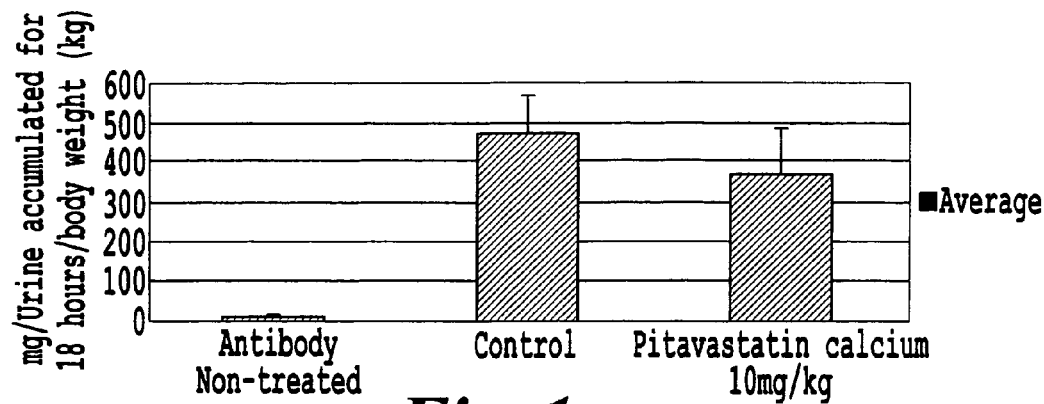
FIG. 1 is a drawing showing a total amount of protein excretion in urine observed when administering pitavastatin calcium alone. Each value in the drawing shows an average value±standard error.

The anti-thrombocytic agent of the present invention means a drug which inhibits adhesion and coagulation of a blood platelet and includes, for example, ticlopidine, cilostazol, ozagrel, beraprost, sarpogrelate, dipyridamole, argatroban, aspirin, dilazep, ethyl icosapentate, limaprost alfadex, alprostadil, alprostadil alfadex, trimetazidine, trapidil and clopidogrel (Japanese Patent Application Laid-Open No. 955/1979), CS-747 (Japanese Patent No. 2683479), AT1015 (Japanese Patent Application Laid-Open No. 3135/1996), SR-46349 (Japanese Patent No. 2562503) and the salts thereof. Among them, preferred are those having an adenosine-enhancing function or a phospholipase-inhibiting function such as dilazep, dipyridamole, trimetazidine, trapidil and the salts thereof, with dilazep and the salts thereof (hydrochloride and the like) being particularly preferred.

The HMG-CoA reductase inhibitor of the present invention includes all of so-called statin-type compounds which have a cholesterol synthesis inhibiting activity and which are known to be a hyperlipidemia therapeutic agent. It includes preferably compounds having a 3,5-dihydroxyheptanoic acid or 3,5-dihydroxy-6-heptenoic acid. Specifically, preferred are compounds described in Japanese Patent Application Laid-Open No. 2240/1982, Japanese Patent Application Laid-Open No. 163374/1982, Japanese Patent Application Laid-Open No. 122375/1981, Japanese Patent Application Laid-open (through PCT) No. 500015/1985, Japanese Patent Application Laid-Open No. 216974/1989, Japanese Patent Application Laid-Open No. 58967/1991, Japanese Patent Application Laid-Open No. 279866/1989 and Japanese Patent Application Laid-Open No. 178841/1993. All of lactone bodies, lactone ring-opened bodies or the salts thereof are included therein. Further, included therein are the hydrates of these compounds and the salts thereof and the solvates thereof with solvents which are acceptable as medicines. When asymmetric carbon atoms are present in these compounds and when they have unsaturated bonds and the stereoisomers thereof are present, all isomers thereof are included therein.

The suited HMG-CoA reductase inhibitor includes, for example, pravastatin ((+)-(3R, 5R)-3,5-dihydroxy-7-[(1S, 2S, 6S, 8S, 8aR)-6-hydroxy-2-methyl-8-[(S)-2-methylbutyryloxy]-1,2,6,7,8,8a-hexahydro-1-naphthyl]heptanoic acid, Japanese Patent Application Laid-Open No. 2240/1982), lovastatin ((+)-(1S, 3R, 7S, 8S, 8aR)-1,2,3,7,8,8a-hexahydro-3,7-dimethyl-8-[2-(2R, 4R)-tetrahydro-4-hydroxy-6-oxo-2H-pyran-2-yl]ethyl]-1-napthyl(S)-2-methylbutyrate, Japanese Patent Application Laid-Open No. 163374/1982), simvastatin ((+)-(1S, 3R, 7S, 8S, 8aR)-1,2,3,7,8,8a-hexahydro-3,7-dimethyl-8-[2-(2R, 4R)-tetrahydro-4-hydroxy-6-oxo-2H-pyran-2-yl]ethyl]-1-napthyl 2,2-dimethylbutyrate, Japanese Patent Application Laid-Open No. 122375/1981), fluvastatin ((±)-(3R*, 5S*, 6E)-7-[3-(4-fluorophenyl)-1-(1-methylethyl)-1H-indol-2-yl]-3,5-dihydroxy-6-heptenoic acid, Japanese Patent Application Laid-Open (through PCT) No. 500015/1985), cerivastatin ((+)-(3R, 5S, 6E)-7-[4-(4-fluorophenyl)-2,6-di-(1-methylethyl)-5-methoxymethylpyridin-3-yl]-3,5-dihydroxy-6-heptenoic acid, Japanese Patent Application Laid-Open No. 216974/1989), atorvastatin ((3R, 5R)-7-[2-(4-fluorophenyl)-5-(1-methylethyl)-3-phenyl-4-phenylaminocarbonyl-1H-pyrrol-1-yl]-3,5-dihydroxyheptanoic acid, Japanese Patent Application Laid-Open No. 58967/1991), pitavastatin ((3R, 5S, 6E)-7-[2-cyclopropyl-4-(4-fluorophenyl)-3-quinolyl]-3,5-dihydroxy-6-heptenoic acid, Japanese Patent Application Laid-Open No. 279866/1989) and rosuvastatin (7-[4-(4-fluorophenyl)-6-isopropyl-2-(N-methyl-N-methylsulfonylamino)pyrimidin-5-yl]-(3R, 5S)-dihydroxy-(E)-6-heptenoic acid, Japanese Patent Application Laid-Open No. 178841/1993) and the salts thereof.

Among them, atorvastatin, rosuvastatin, pitavastatin and the salts thereof are more preferred, and pitavastatin and the salts thereof (a sodium salt, a calcium salt and the like) are more preferred.

The anti-thrombocytic agent and the HMG-CoA reductase inhibitor each described above can be produced by publicly known methods in addition to the methods described in the published patent applications described above.

The drug of the present invention is used by combining the anti-thrombocytic agent with the HMG-CoA reductase inhibitor each described above. As shown in examples described later, the drug has a function to notably inhibit the total protein excretion amount in urine in a progressive anti-Thy-1 nephritic rat which is a glomerular disease model as compared with a case where the anti-thrombocytic agent and the HMG-CoA reductase inhibitor are each administered solely.

Accordingly, the drug of the present invention is effective for prevention or therapy of a glomerular disease of animals, particularly prevention or therapy of a glomerular disease of mammals including human beings. The examples of such glomerular disease include chronic glomerular nephritis such as. IgA nephropathy, focal glomerulonephritis, membranous nephropathy and membranous proliferative nephropathy.

A use form of the anti-thrombocytic agent and the HMG-CoA reductase inhibitor in the preventive or therapeutic agent of the present invention for a glomerular disease shall not specifically be restricted, and both drugs may be administered at the same time or may be separately administered leaving an interval.

That is, the anti-thrombocytic agent and the HMG-CoA reductase inhibitor may be mixed with a diluent, a filler and the like which can pharmaceutically be allowed to prepare a single preparation or the drugs may separately be turned into preparations to prepare a set (kit). When both drugs are turned into separate preparations, the dosage forms may be different from each other.

The preventive or therapeutic agent of the present invention for a glomerular disease can have various dosage forms according to uses thereof. Examples include a powder, a granule, a particle, a dry syrup, a tablet, a capsule and an injection form.

These preparations can be produced according to a conventional method by suitably mixing, diluting or dissolving with medicinal additives such as an excipient, a disintegrating agent, a binder, a glossing agent, a diluent, a buffer solution, an isotonizing agent, an antiseptic agent, a wetting agent, an emulsifier, a dispersant, a stabilizing agent and a dissolution aid which are pharmaceutically allowable according to the formulation forms thereof.

For example, the powder preparation can be prepared by adding, if necessary, a suitable excipient, glossing agent and the like to the active ingredients (the anti-thrombocytic agent and/or the HMG-CoA reductase inhibitor) and admixing them well, and the tablet can be prepared by adding, if necessary, a suitable excipient, disintegrating agent, binder, glossing agent and the like and making a tablet. Further, the tablet can be provided with a coating to prepare a film-coated tablet and a sugar-coated tablet.

Also, the injection preparation can have the forms of a liquid formulation (an aseptic solution or a non-aqueous solution), an emulsion and a suspension, and a non-aqueous carrier, a diluent, a solvent or a vehicle used therefore includes, for example, propylene glycol, polyethylene glycol, vegetable oil such as olive oil and organic acid esters such as ethyl oleate which can be injected. Further, the above composition can suitably be blended with adjuvants such as an antiseptic agent, a wetting agent, an emulsifier and a dispersant.

A content of the anti-thrombocytic agent and the HMG-CoA reductase inhibitor in the preventive or therapeutic agent of the present invention for a glomerular disease may suitably be selected according to the formulations, and it is about 1 to 50 mass %, preferably about 10 to 50 mass % in the case of the anti-thrombocytic agent and about 0.1 to 10 mass %, preferably about 0.5 to 5 mass % in the case of the HMG-CoA reductase inhibitor.

In the present invention, the anti-thrombocytic agent and the HMG-CoA reductase inhibitor which have separately been formulated as described above can be administered at the same time or at intervals difference, and in the latter case, an administering frequency of the respective components may be different.

A dosage of the preventive or therapeutic agent of the present invention for a glomerular disease is suitably selected according to the kind and the symptom of the glomerular disease, and are 1 to 1000 mg, preferably 10 to 500 mg a day in the case of the anti-thrombocytic agent and 0.1 to 100 mg, preferably 1 to 50 mg a day in the case of the HMG-CoA reductase inhibitor. This dosage can be divided into once to several times a day.

EXAMPLES

The present invention shall be explained below in more detail with reference to examples.

Example 1

Pharmacological Test to a Progressive Anti-Thy-1 Nephritic Rat

Wistar female rats (5 weeks of age, purchased from Japan SLC Co., Ltd.) were quarantined and acclimatized for 4 days and then used for the test. First, a right kidney of the rat was removed through a flank incision under anesthesia with pentobarbital. After 2 weeks passed, an anti-Thy-1 antibody (monoclonal antibody 1-22-3; purchased from Panafarm Laboratories Co., Ltd.) was intravenously administered (500 μg/rat) into the tail vein to thereby bring about progressive renal damage, and the following tests 1 to 3 were immediately investigated.

Test 1: pitavastatin calcium (10 mg/kg, N=7) suspended in a 0.5% sodium carboxymethyl cellulose aqueous solution was continuously orally administered for 10 weeks.
Control group (antibody-treated and compound-non-administered group): N=8, an antibody-non-treated group: N=6.
Test 2: dilazep hydrochloride (10 mg/kg) dissolved in a physiological saline was continuously intraperitoneally administered for 10 weeks.
Control group (antibody-treated and compound-non-administered group): N=8, an antibody-non-treated group: N=6.
Test 3: two drugs were administered in combination for 10 weeks by orally administering pitavastatin calcium (5 mg/kg, N=10) suspended in a 0.5% sodium carboxymethyl cellulose aqueous solution and immediately thereafter intraperitoneally administering dilazep hydrochloride (5 mg/kg, N=10) dissolved in a physiological saline.
Control group (antibody-treated and compound-non-administered group): N=10, an antibody-non-treated group: N=6.

In each test, after administering the drugs for 10 weeks, urine was taken for 18 hours by means of a metabolic cage (Sugiyama Gen Co., Ltd.) to measure the total amount of protein excretion in urine. The results thereof are shown in Tables 1 to 3.

Figure 2:
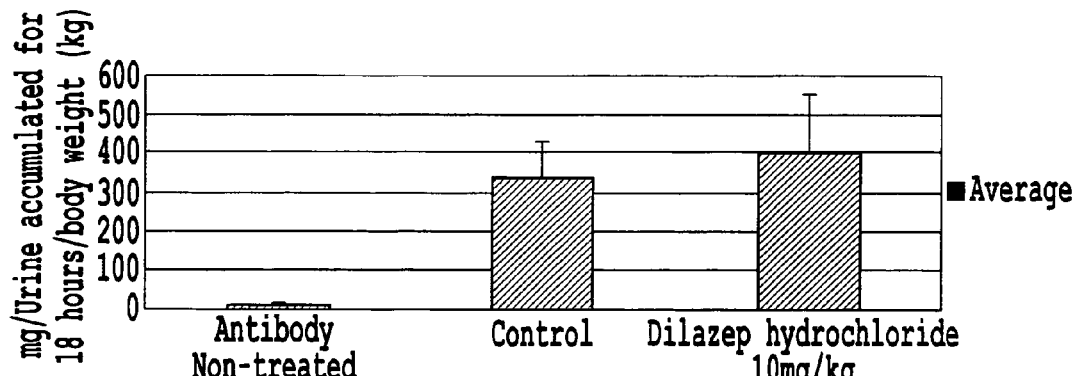
FIG. 2 is a drawing showing a total amount of protein excretion in urine observed when administering dilazep hydrochloride alone. Each value in the drawing shows an average value±standard error.

The total amount of protein excretion in urine after administering pitavastatin calcium (10 mg/kg) for 10 weeks was almost the same as that of the compound-non-administered group in the control, and an effect of pitavastatin calcium was not observed (FIG. 1). Further, the total amount of protein excretion in urine after administering dilazep hydrochloride (10 mg/kg) for 10 weeks also was almost the same as that of the compound-non-administered group in the control, and an effect of dilazep hydrochloride was not observed (FIG. 2).

Figure 3:
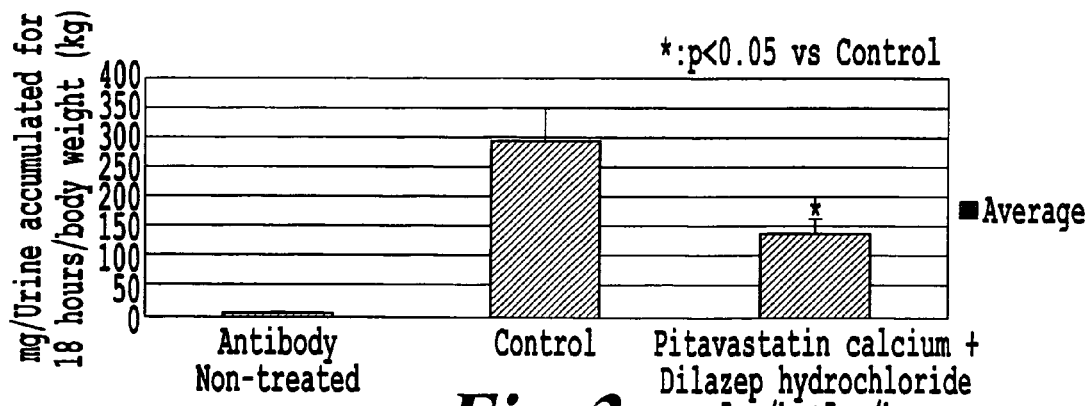
FIG. 3 is a drawing showing a total amount of protein excretion in urine observed when administering pitavastatin calcium and dilazep hydrochloride in combination. Each value in the drawing shows an average value±standard error.

In contrast with this, the total amount of protein excretion in urine after administering pitavastatin calcium (5 mg/kg) and dilazep hydrochloride (5 mg/kg) in combination for 10 weeks was observed to be significantly inhibited as compared with those of the compound-non-administered groups in the controls (FIG. 3).

Formulation Example 1 Tablet

A tablet having the following composition per tablet was produced by the following method.

TABLE 1

| | |
|---|---|
| Pitavastatin calcium | 2 mg |
| Dilazep hydrochloride | 100 mg |
| Lactose | 70 mg |
| Low-substituted hydroxypropyl cellulose | 20 mg |
| Hydroxypropyl cellulose | 6 mg |
| Magnesium stearate | 2 mg |
| Total | 200 mg |

Pitavastatin calcium to hydroxypropyl cellulose were mixed to prepare a homogeneous powder mixture, and a suitable amount of purified water was added thereto to granulate the mixture by a stirring granulation method, whereby a tableted granule was prepared. Magnesium stearate was mixed with this tableted granule, and the mixture was tableted to obtain a tablet containing pitavastatin calcium and dilazep hydrochloride.

INDUSTRIAL APPLICABILITY

The preventive or therapeutic agent of the present invention for a glomerular disease is useful for prevention and therapy of various glomerular diseases including chronic glomerular nephritis such as IgA nephropathy, focal glomerulonephritis, membranous nephropathy and membranous proliferative nephropathy.

What is claimed is:
1. A composition comprising:
an anti-thrombocytic agent and
an HMG-CoA reductase inhibitor
in an amount sufficient to treat chronic glomerular nephritis;
wherein the anti-thrombocytic agent is selected from the group consisting of dilazep, dipyridamole and; or salts thereof; and
wherein the HMG-CoA reductase inhibitor is pitavastatin; or salts thereof.
2. The composition of claim 1,
wherein the anti-thrombocytic agent is dilazep or a salt thereof.
3. The composition of claim 1,
wherein the HMG-CoA reductase inhibitor is pitavastatin.
4. The composition of claim 1,
wherein the HMG-CoA reductase inhibitor is a salt of pitavastatin.
5. The composition of claim 1,
wherein the HMG-CoA reductase inhibitor is present in an amount ranging from 0.5 to 5 mass % and the anti-thrombocytic agent is present in an amount ranging from 10 to 50 mass %.
6. The composition of claim 1,
wherein the pitavastatin or a salt thereof is present in an amount ranging from 0.1 to 10 mass % and the dilazep or a salt thereof is present in an amount ranging from 1 to 50 mass %.
7. The composition of claim 1, which contains the anti-thrombocytic agent and the HMG-CoA reductase inhibitor in a single formulation.
8. A kit comprising the anti-thrombocytic agent and the HMG-CoA reductase inhibitor of claim 1 as separate formulations.
9. The composition of claim 1, further comprising at least one pharmaceutically acceptable carrier.

10. A method for making the composition of claim 1 comprising admixing said anti-thrombocytic agent and said HMG-CoA reductase inhibitor in amounts sufficient to treat chronic glomerular nephritis.

11. A method for treating a chronic glomerular nephritis, which comprises administering to a subject in need thereof an effective amount of a composition comprising: an anti-thrombocytic agent and an HMG-CoA reductase inhibitor in an amount sufficient to treat chronic glomerular nephritis; wherein the anti-thrombocytic agent is selected from the group consisting of dilazep and dipyridamole, or salts thereof and wherein the HMG-CoA reductase inhibitor is pitavastatin, or salts thereof.

12. The method of claim 11, wherein the anti-thrombocytic agent and HMG-CoA reductase inhibitor are administered as a single preparation.

13. The method of claim 11, wherein the anti-thrombocytic agent and HMG-CoA reductase inhibitor are separately administered.

14. The method of claim 11, wherein the anti-thrombocytic agent is dipyridamole or a salt thereof.

15. The method of claim 11, wherein the anti-thrombocytic agent is dilazep or a salt thereof.

16. The method of claim 11, wherein the HMG-CoA reductase inhibitor is pitavastatin.

17. The method of claim 11, wherein the HMG-CoA reductase inhibitor is a salt of pitavastatin.

18. The method of claim 11, wherein the HMG-CoA reductase inhibitor is present in an amount ranging from 0.1 to 10 mass % and the anti-thrombocytic agent is present in an amount ranging from 1 to 50 mass %.

19. The method of claim 11, wherein said subject exhibits proteinuria.

20. The composition of claim 1, wherein the anti-thrombocytic agent is dipyridamole or a salt thereof.

21. The composition of claim 20, wherein the pitavastatin or salt thereof is present in an amount ranging from 0.1 to 10 mass % and the dipyridamole or a salt thereof is present in an amount ranging from 1 to 50 mass %.

* * * * *